United States Patent [19]

Grub et al.

[11] Patent Number: 6,087,299
[45] Date of Patent: Jul. 11, 2000

[54] SILVER-CONTAINING SUPPORTED CATALYSTS AND CATALYST INTERMEDIATES, PROCESSES FOR THEIR PREPARATION AND THEIR USE

[75] Inventors: Joachim Grub, Dormagen; Werner Volprecht, Bergheim; Matthias Baum; Alfred Reimer, both of Dormagen, all of Germany

[73] Assignee: EC Erdolchemie GmbH, Germany

[21] Appl. No.: 09/237,113

[22] Filed: Jan. 26, 1999

[30] Foreign Application Priority Data

Jan. 31, 1998 [DE] Germany ............ 198 03 890

[51] Int. Cl.[7] .............. B01J 23/50; B01J 23/02; C07D 301/03; C07D 301/10; C07D 303/04
[52] U.S. Cl. ............ 502/347; 502/344; 502/348; 549/512; 549/513; 549/518; 549/523; 549/524; 549/534; 549/537
[58] Field of Search ................. 502/344, 347, 502/348; 549/512, 513, 518, 523, 524, 534, 537

[56] References Cited

U.S. PATENT DOCUMENTS

| | | |
|---|---|---|
| 2,404,438 | 7/1946 | Evans et al. . |
| 4,066,575 | 1/1978 | Winnick . |
| 4,305,844 | 12/1981 | Vangermain et al. . |
| 4,400,308 | 8/1983 | Alter et al. . |
| 4,908,343 | 3/1990 | Bhasin ............... 502/218 |
| 5,173,469 | 12/1992 | Wunde et al. . |
| 5,281,728 | 1/1994 | Wunde et al. . |
| 5,625,084 | 4/1997 | Pitchai et al. ............ 549/536 |

FOREIGN PATENT DOCUMENTS

| | | |
|---|---|---|
| 428 845 | 5/1991 | European Pat. Off. . |
| 1257352 | 12/1971 | United Kingdom . |
| 1413251 | 11/1975 | United Kingdom . |
| 1563051 | 3/1980 | United Kingdom . |

OTHER PUBLICATIONS

Ralph Landau and Rex E. Lidow, Ethylene Oxide, Chapter 7 in *Ethylene and its Industrial Derivatives*, Ed. S. A. Miller and Ernest Benn, London, pp. 513–638 London (1963). No Month Available.

D. J. Hucknall, The Catalytic Oxidation of Ethylene, Chapter 2 in *Selective Oxidation of Hydrocarbons*, Academic Press, London, pp. 6–22 (1974). No Month Available.

McNaught, Kemball and Leach, Exchange Reactions with $D_2O$, pp. 100–105, and A. Ekstrom, G.E. Batley, and D.A. Johnson, Studies of Topochemical Heterogeneous Catalysis, pp. 106–114, both in *Journal of Catalysis*, vol. 34, 100–114 (1974). No Month Available.

Stephen Brunauer, P.H. Emmett, and Edward Teller, Adsorption of Gases in Multimolecular Layers, in *The Journal of the American Chemical Society*, vol. 60, pp. 309–316 (1938). No Month Available.

Derwent WPAT English Abstract for DE 23 00 512 (See Ref. D) No Dates for Abstracts.

Derwent WPAT English Abstract for DE 19 20 976 (See Ref. E) No Dates for Abstracts.

Derwent WPAT English Abstract for DE 27 33 688 (See Refs. C and F) No Dates for Abstracts.

Derwent WPAT English Abstract for EP 38 446 No Dates for Abstracts.

*Primary Examiner*—Elizabeth D. Wood
*Attorney, Agent, or Firm*—Connolly Bove Lodge & Hutz LLP

[57] ABSTRACT

The present invention relates to silver-containing and optionally promoter-containing supported catalysts and catalyst intermediates, processes for their preparation and their use for preparing alkylene oxides by oxidation of alkenes with oxygen. The catalysts are prepared by treatment of a support with a lactic acid containing silver ions, nitrate ions and optionally promoter metal ions, drying, predecomposition in a virtually oxygen-free atmosphere and subsequent activation by heating in an oxygen-containing atmosphere while precisely controlling the temperature conditions and the feeding-in of oxygen. The catalyst intermediates obtainable by treatment, drying and only predecomposition can be activated in a temporally and physically separate process step to form the actual catalysts. Suitable promoters are alkaline earth metal compounds and/or alkali metal compounds. High activities and high selectivities are achieved when using the catalysts of the invention for preparing alkylene oxides.

18 Claims, No Drawings

SILVER-CONTAINING SUPPORTED CATALYSTS AND CATALYST INTERMEDIATES, PROCESSES FOR THEIR PREPARATION AND THEIR USE

BACKGROUND OF THE INVENTION

1. Field of the Invention

The invention relates to silver-containing and optionally promoter-containing supported catalysts and catalyst intermediates, processes for their preparation and their use for preparing alkylene oxides by direct oxidation of alkenes using air or oxygen-containing gases.

2. Description of the Prior Art

For the industrial preparation of alkylene oxides, use is nowadays made of the direct oxidation of alkenes using air or using gases containing molecular oxygen in the presence of a silver-containing catalyst. Since alkylene oxides, particularly ethylene oxide, have great economic importance as basic chemicals for numerous downstream products, many attempts have been made to improve the performance of the catalysts used. The numerous proposed modifications for improving the activity and the selectivity concern the support material used, the process for preparing the catalysts and the addition of promoters (R. Landau and R. E. Lidow, "Ethylene and its industrial derivatives" S. A. Miller and Ernest Benn, London 1963; D. J. Hucknall "Selective oxidations of hydrocarbons" Academic Press, London 1974; J. of catalysis 34, 100–114 (1974)).

The operating temperature of a catalyst for preparing alkylene oxides is particularly important. It is desirable to have catalysts which have a high activity and selectivity at a low temperature. A low operating temperature results in, for example, a longer operating life of the catalyst, which is of great importance for the industrial process. Furthermore, the formation of by-products, for example the formation of the isomeric acetaldehyde and of formaldehyde in the preparation of ethylene oxide, is significantly less at lower temperatures and thus makes it easier to remove these impurities during the work-up of the alkylene oxide to give a pure starting chemical which satisfies all requirements.

Apart from the disadvantages indicated above, high operating temperatures often lead to undesired secondary reactions at the outlet of the catalyst bed. The reaction products formed here can damage the performance of the catalyst and also lead to undesirable production stoppages in commercial plants. High operating temperatures also favour the occurrence of uncontrollable hot spots which can cause not only technical malfunctions but also can adversely affect the safety of the preparation process.

The operating temperature of a catalyst can be influenced by the addition of promoters and by the preparation process. Promoters which have been found to be particularly advantageous are added oxides, hydroxides and peroxides of the alkali metals and alkaline earth metals (U.S. Pat. No. 2,404, 438). A series of patent applications, for example German Offenlegungsschrift 23 00 512 describes, in particular, the addition of the heavy alkali metals as promoters. In further patent applications, for example German Auslegeschrift 19 20 976 places particular emphasis on barium as promoter among the alkaline earth metals.

German Offenlegungsschrift 27 33 688 claims a process for preparing a silver-containing supported catalyst in which a support material is impregnated with a silver compound, the impregnated particles are activated by at least partial conversion into elemental silver and, finally, at least one of the alkali metals potassium, rubidium and caesium is deposited on the catalyst prepared in this way. The silver-containing impregnation solution preferably contains a barium salt.

All previously described catalysts have the relatively high operating temperature of 230–260° C.

EP-A 38 446 (=U.S. Pat. No. 4,400,308) describes silver-containing supported catalysts in whose preparation a support is impregnated with an Ag-containing lactic acid. After drying, the lactic acid is predecomposed in a defined manner in two stages in an oxygen-free atmosphere and is finally decomposed in an oxygen-containing atmosphere, likewise in a defined manner, during the activation of the catalyst. Such catalysts allow operating temperatures for the preparation of ethylene oxide which at from 160 to 230° C. are significantly lower than those of the prior art; the ethylene oxide selectivities are from 80 to 81%.

SUMMARY OF THE INVENTION

In a further development of the catalyst preparation of EP '446, it was found that a content of nitrate anions in the impregnation solution for the catalyst support, which otherwise continues to contain lactic acid, silver ions and optionally promoter metal ions, gives catalysts which allow further increased ethylene oxide selectivities to be achieved. This finding is surprising in view of EP '446 since a non-oxidizing atmosphere is created during the predecomposition by the absence of oxygen and, according to Example 1 of EP '446 nitrate-free AgO is used.

We have now found silver-containing and optionally promoter-containing supported catalysts prepared by a) treating a support having a specific surface area of not more than 1.5 $m^2/g$ with a lactic acid containing silver ions, nitrate ions and optionally promoter metal ions, b) drying the treated support obtained as described in a) and predecomposing the lactic acid and nitric acid which are present in free form and in the form of their anions in a virtually oxygen-free atmosphere, with the drying being carried out at a temperature of from about 50 to about 120° C. and the predecomposition being carried out in the temperature range from about 140 to about 220° C. and optionally then in the temperature range from about 400 to about 500° C., setting a heating rate of from 70 to 150° C./hour for the transition between the two temperature ranges in the case of the two-stage predecomposition, and c) activating the catalyst intermediates obtained as described in b) by heating in an oxygen-containing atmosphere, with the temperature being increased from at least 130° C. to a maximum of 450° C. at a heating rate of from about 3 to about 8° C./hour and the oxygen content being increased from about 0.4 to about 21% by volume in such a way that a $CO_2$ content of 2% by volume, preferably 1% by volume, is not exceeded in the waste gas from the activation step.

DESCRIPTION OF THE PREFERRED EMBODIMENTS

The catalysts of the invention can be ones with or without promoters. If promoters are present in the catalysts of the invention, promoters can be alkaline earth metal compounds, for example compounds of calcium, strontium or barium, and/or alkali metal compounds, for example compounds of lithium, sodium, potassium, rubidium or caesium. Preferred promoters are barium and/or caesium and/or potassium compounds. Catalysts of the invention can contain compounds of barium or of caesium or potassium or compounds of both metals. Particularly preferred catalysts according to the invention are those containing barium and caesium and potassium compounds.

Examples of amounts of the active metals are the following, calculated as metals or metal ions and based on the total weight of the finished catalyst: for silver, an amount of from about 7 to about 30% by weight, preferably from 10 to 20% by weight, particularly preferably from 12 to 18% by weight; if alkaline earth metal compounds are present as promoters, for these an amount of from about 0.05 to about 0.5% by weight, preferably from 0.07 to 0.3% by weight, particularly preferably from 0.08 to 0.15% by weight; if alkali metals are present as promoters, for these an amount of from about 0.001 to about 1% by weight, preferably from 0.005 to 0.5% by weight, particularly preferably from 0.01 to 0.05% by weight; if alkaline earth metals and alkali metals are present together as promoters, they can be present, independently of one another, in the amounts indicated for each.

Support materials for the catalysts of the invention are porous, heat-resistant catalyst support materials which are inert under the conditions of catalyst preparation and of catalyst use. The support material has a macroporous structure having a specific surface area of not more than 1.5 $m^2/g$, for example from 0.01 to 1.5 $m^2/g$, preferably from 0.1 to 1.1 $m^2/g$, particularly preferably from 0.5 to 1 $m^2/g$. The porosity of the support material is, for example, from 40 to 70%, preferably from 45 to 60%. The pore diameter is, for example, in the range from 0.1 to 100 $\mu$m. Suitable support materials having the physical properties mentioned are those of natural or synthetic origin. for example α-aluminium oxide, silicon carbide, synthetic or natural zeolites, magnesium oxide, zirconium oxide or ceramic materials, preferably α-aluminium oxide.

The catalysts of the invention are characterized in that the active metals to be applied to the support are applied from a solution which contains lactic acid and nitric acid in free form or in the form of their anions. The amount of anions (equivalents) of lactic and nitric acid is at least as great as the sum of equivalents of the active metals; this represents a 100% value for the acid anions. The total range of anions of both acids (lactic and nitric acid) is from 100 to 200%, preferably from 110 to 150%, of the metal equivalents in the above-defined way. Within the total amount of the two acids, their ratio to one another is such that from 1 to 30 mol % (=equivalent-%), preferably from 3 to 25 mol %, of nitrate anion are present per 100 mol % (=equivalent-%) of lactic acid. The nitrate anion can be added in various forms to the solution of active metals to be applied to the support. Thus, free nitric acid ($HNO_3$) or $NH_4NO_3$ can be added to a lactic acid solution prepared as described in EP '446. Furthermore, it is possible to add amounts of the active metals in the form of their nitrate, i.e. part of the silver cation in the form of $AgNO_3$, alkaline earth metal or alkali metal in the form of their nitrates, e.g. $Ca(NO_3)_2$, $Sr(NO_3)_2$, $Ba(NO_3)_2$, $LiNO_3$, $NaNO_3$, $KNO_3$, $RbNO_3$ or $CsNO_3$ or a plurality thereof. The support can likewise be treated with $HNO_3$ or $NH_4NO_3$ solution before application of the solution of the active metals, or the support can be treated with $HNO_3$ or $NH_4NO_3$ solution after application of the solution of the active metals, if desired after a drying step, the amount of nitrate anion in each case corresponding to the above definition. The respective application is carried out in a manner known to those skilled in the art, e.g. by impregnation or spraying-on.

The invention further relates to a process for preparing silver-containing and optionally promoter-containing supported catalysts by treatment of a support with a solution containing silver and optionally promoter metals, subsequent drying and calcination, which is characterized in that
  a) a support having a specific surface area of not more than 1.5 $m^2/g$ is treated in a manner known per se with lactic acid containing silver ions, nitrate ions and optionally promoter metal ions,
  b) the impregnated support obtained as described in a) is dried in a virtually oxygen-free atmosphere at from about 50 to about 120° C. and the lactic acid and nitric acid which are present in ionic or free form are predecomposed in the temperature range from about 140 to about 220° C. and, if desired, then in the temperature range from about 400 to about 500° C. in a virtually oxygen-free atmosphere, with a heating rate of from 70 to 150° C. per hour being set for the transition between the two temperature ranges in the case of the two-stage predecomposition, and
  c) the catalyst intermediate obtained as described in b) is activated by heating in an oxygen-containing atmosphere, with the temperature being increased from at least 130 to a maximum of 450° C. at a heating rate of from about 3 to about 8° C./hour and the oxygen content being increased from about 0.4 to about 21% by volume in such a way that a $CO_2$ content of 2% by volume, preferably 1% by volume, is not exceeded in the waste gas from the activation step.

The support for the catalyst preparation process of the invention is, for example, one of the above-described supports having the physical properties described there. Preference is given to using α-aluminium oxide having the above-described properties as support.

As lactic acid, it is possible to use the racemate containing equal amounts of the two enantiomers or a lactic acid containing an excess of one of the enantiomers. Preference is given to using a lactic acid which contains racemate plus an excess of one of the enantiomers. For this preferred form, it is possible to use, for example, a lactic acid which contains at least 50% by weight of one enantiomer, preferably at least 50% by weight of the L(+) form, particularly preferably at least 80% by weight of the L(+) form, the remainder in each case consisting of the racemate of the two enantiomers. Lactic acid can also be used in the form of the lactate of one or more of the active metals or at least partly as ammonium lactate.

The lactic acid used according to the invention for treating the catalyst support contains silver in the form of silver ions. Such a silver-containing lactic acid may be prepared, for example, by introduction of silver oxide, silver carbonate or separately prepared silver lactate into the lactic acid. Of course, it is also possible to use other thermally decomposable silver compounds for this purpose. Within the above definition, it is also possible to use part of the silver in the form of $AgNO_3$. Preference is given to the introduction of silver oxide, particularly preferably freshly precipitated silver oxide, into the lactic acid. The lactic acid used for the treatment contains, for example, from 25 to 45% by weight, preferably from 28 to 40% by weight, of silver ions, based on the total amount of treatment liquid. The desired silver ion content can, if appropriate, be set to the desired value before the treatment by addition of distilled water, concentrated or dilute $HNO_3$ or variously concentrated $NH_4NO_3$ solutions to the treatment liquid. The silver-containing lactic acid is prepared at a temperature of, for example, from 40 to 70° C. After the addition of the silver compound is complete, an amount of about 1 ml of 30% strength by weight hydrogen peroxide solution/100 g of silver ions is advantageously added to the lactic acid.

If alkaline earth metal ions and/or alkali metal ions are added as promoters, this may be an addition of hydroxides, carbonates or nitrates, of one or more alkaline earth metals and/or alkali metals. For the alkaline earth metals, mention may be made, for example, of the following compounds: calcium hydroxide, calcium carbonate, calcium nitrate, strontium hydroxide, strontium carbonate, strontium nitrate, barium hydroxide, barium carbonate, barium nitrate, preferably barium hydroxide, barium carbonate or barium nitrate. Examples of alkali metal compounds which may be mentioned are: lithium hydroxide, lithium carbonate, lithium nitrate, sodium hydroxide, sodium carbonate, sodium nitrate, potassium hydroxide, potassium carbonate, potassium nitrate, rubidium hydroxide, rubidium carbonate, rubidium nitrate, caesium hydroxide, caesium carbonate, caesium nitrate, preferably caesium hydroxide, caesium carbonate or caesium nitrate. The amount of alkaline earth metal compounds is, for example, from about 0.5 to 3 g, preferably from 0.7 to 2 g/100 g of 100% pure lactic acid. For the alkali metal compounds, the amount is, for example, from 30 to 300 mg, preferably from 70 to 200 mg/100 g of 100% pure lactic acid.

The amount of lactic acid containing the silver, the nitrate anion and, if desired, the promoter metals which has been made up and the amounts of the active metals present therein depend of course on the desired amount of active metals on the finished catalyst within the abovementioned ranges for the individual metals and also on the porosity of the catalyst support used. However, these relationships can be determined in simple preliminary experiments. The volume of lactic acid solution used for the treatment is made such that the catalyst support is completely sprayed or impregnated and, if appropriate, only little impregnation liquid drips from the impregnated catalyst after impregnation. For example, the amount of lactic acid solution which drips from the impregnated support may be from about 5 to 30% by volume, preferably from 10 to 20% by volume, of the total lactic acid solution used. This amount can be taken into account beforehand in a known manner.

In a preferred variant of the process of the invention, soluble, readily decomposable, non-reducing organic compounds such as sugar alcohols (sorbitol, mannitol), polyhydroxy acids, sucrose, starch or trimellitic acid, preferably sucrose, can be added to the lactic acid containing the silver, nitrate anions and, if desired, promoter metals. These organic compounds are added, for example, in an amount of from about 30 to about 45 g/100 g of 100% pure lactic acid.

The order of addition of the individual components of the treatment liquid can, for example, be as follows: initial charging of the lactic acid, if desired introduction of the alkaline earth metal compound, if desired introduction of the alkali metal compound, introduction of the silver compound, addition of the nitrate anion in one of the abovementioned forms, advantageously addition of hydrogen peroxide and if desired addition of the organic compound described. The introduction of the compounds mentioned into the initially charged lactic acid can, however, also be carried out in any other order.

An above-described catalyst support is treated with the treatment liquid obtained in the manner described by dipping into the solution one or more times or by spraying. The above-described excess of impregnation liquid is allowed to drip off freely and the treated support is then placed in a convection oven.

A virtually oxygen-free atmosphere is maintained in this convection oven. For the purposes of the present invention, a virtually oxygen-free atmosphere is one containing not more than 100 ppm by volume of $O_2$, for example from 1 to 100 ppm by volume, preferably from 1 to 20 ppm by volume. As inert gas for the virtually oxygen-free atmosphere, it is possible to use, for example, nitrogen, carbon dioxide or noble gas, preferably nitrogen, which is oxygen-free or has an oxygen content in the range mentioned.

For drying the treated support, the convection oven described is set to a temperature of from about 50 to about 120° C., preferably from 90 to 120° C., particularly preferably from 100 to 110° C. The duration of the drying step is dependent on the amount of support treated, the amount of water in the treatment liquid, the amount of circulated air and the temperature within the given range. This time can be in the range from about 1 to about 4 hours.

The treated and dried catalyst support is then subjected to predecomposition of the organic constituents, likewise in a virtually oxygen-free atmosphere. For this purpose, the temperature is increased to one in the range from about 140 to about 220° C., preferably from 140 to 160° C., particularly preferably from 145 to 155° C., and held in this range for from about ½ to about 2 hours. If desired, a second predecomposition temperature is then set at a heating rate of from 70 to 150° C., preferably from 90 to 110° C., per hour. This second temperature is, for example, in the range from about 400 to about 500° C., preferably from 430 to 470° C., and is, like the first predecomposition temperature, held for from about ½ to about 2 hours. The mode of action of the nitrate addition and the two separate temperature ranges described has not yet been conclusively examined. However, it can be assumed that in the first of the predecomposition temperature ranges indicated, a gentle decomposition of the organic material is commenced with a growing together of silver crystals to form larger units being substantially avoided. In the second of the predecomposition temperature ranges mentioned, a further decomposition of the organic material and removal of the volatile pyrolysis products formed can then be assumed. If promoter metals are present in the catalyst, it can also be assumed that solid-state reactions between the promoter metal compounds and the silver take place in the second of the temperature ranges mentioned.

After this predecomposition according to the invention, the catalyst intermediate obtained still contains from about 0.5 to 8, preferably from 1 to 8, particularly preferably from 2 to 5,% by weight of carbon, based on the total weight of the catalyst intermediate.

Subsequent to the described predecomposition, the catalyst intermediate is activated by heating in an oxygen-containing atmosphere. For this heating, the catalyst intermediate is first brought to a temperature of not more than 130° C. in the virtually oxygen-free atmosphere and then treated in the presence of oxygen at a temperature rising steadily from at least 130° C. to a maximum of 300° C., with a heating rate of from about 3 to about 8° C. per hour having to be maintained. The temperature increase described is preferably carried out from at least 140 to a maximum of 260° C., particularly preferably from at least 150 to a maximum of 240° C.

At the beginning of the heating programme described, the virtually oxygen-free atmosphere is replaced by an atmosphere initially containing about 0.4% by volume of oxygen, with the balance to 100% by volume being able to consist, for example, of the abovementioned inert gases. This oxygen content in the activation atmosphere is then slowly increased from the abovementioned about 0.4% by volume to about 21% by volume in such a way that a $CO_2$ content of 2% by volume, preferably 1% by volume, is not exceeded in the waste gas from this activation step. The duration of this activation according to the invention can be derived from the heating rate and the selected temperature interval and is, for example, from 12 to 30 hours.

In a variant of the predecomposition/activation procedure described, only the first predecomposition step can be carried out in the temperature range from 140 to 200° C. with omission of the second predecomposition step and, after cooling to 130° C. or below, the second predecomposition can be combined with the described activation in the manner described for the activation.

The predecomposition and activation according to the invention can each be carried out, independently of one another, at atmospheric pressure, subatmospheric pressure or superatmospheric pressure. Suitable pressures are, for example, in a range from 0.1 to 50 bar, preferably from 1 to 20 bar, particularly preferably from 5 to 15 bar.

In the process of the invention, it is not necessary for the predecomposition and the activation to form the finished catalyst to be carried out in direct succession. For example, it is also possible, after going through the second predecomposition temperature range in a virtually oxygen-free atmosphere, to cool the resulting catalyst intermediate to about 70–80° C. in a virtually oxygen-free atmosphere and then to take the intermediate from the convection oven. This catalyst intermediate contains, as described, from about 0.5 to about 8, preferably from 1 to 8, particularly preferably from 2 to 5,% by weight of carbon, based on the total weight of this intermediate. This intermediate can be stored indefinitely without adversely affecting the catalytic activity of the active silver catalyst which can be prepared therefrom. Before use, the intermediate is activated to form the final catalyst. This activation can be carried out, for example, in the convection oven described under the conditions described.

However, the activation of the catalyst intermediate can also be carried out in the reactor in which the finished catalyst after the activation is used for the predetermined catalytic reaction, for example in a reactor for preparing alkylene oxides, provided that such a reactor makes it possible to adhere to the above-described activation conditions in respect of temperatures and metering in of oxygen. This latter procedure for activating the catalyst intermediate is preferred.

For example, the catalyst intermediate, if desired after relatively long intermediate storage, is introduced into the tube system known per se of a fixed-bed reactor for the preparation of ethylene oxide. The intermediate is then heated to at least 130° C. in a virtually oxygen-free inert gas stream. Heating can be achieved by means of the inert gas stream, but can also be aided by a heat-transfer medium circulating around the tubes. The temperature is then increased as described above at the heating rate described and an oxygen concentration of initially about 0.4% by volume is set. The gas stream leaving the reactor is continually monitored for its $CO_2$ content which, according to the invention, should not exceed 2% by volume, preferably 1% by volume. While adhering to this $CO_2$ content, the oxygen content of the gas entering the reactor is then increased in the manner described to about 21% by volume. If after reaching the upper temperature value of the activation step the $CO_2$ content of the gas leaving the reactor has dropped to a value of less than 0.3% by volume, for example about 0.1% by volume, the activation of the catalyst is ended. The temperature in the reactor is then lowered to the temperature required for the preparation of alkylene oxide, for example the temperature required for the preparation of ethylene oxide, and the preparation of alkylene oxide, for example ethylene oxide, is commenced by passing the gas mixture known to those skilled in the art for the preparation of alkylene oxide into the catalyst bed.

The invention therefore also provides intermediates for silver-containing and optionally promoter-containing supported catalysts which are characterized by the above-described impregnation, drying, predecomposition and subsequent cooling in a virtually oxygen-free atmosphere to a temperature of about 70–80° C. according to the invention. The intermediate is preferably prepared using the two-stage predecomposition described.

The invention likewise provides a process for preparing such catalyst intermediates which is characterized in the same way by the above-described impregnation, drying, predecomposition and cooling in a virtually oxygen-free atmosphere to about 70–80° C. according to the invention.

In agreement with EP '446 and in comparison with the catalysts obtained by previously customary preparation processes, the catalysts of the invention display significant differences in terms of their specific surface area, the morphology of the silver surface and the particle size of the silver crystallites. Thus, the specific surface area measured by the BET method (J. Am. Chem. Soc. 60, 309–316 (1938)) is about 0.2–0.8 $m^2$/g compared with a specific surface area of less than 0.1 $m^2$/g in the case of catalysts which have been prepared by customary processes. Microscropic examination shows a uniform, continuous particle structure with spherical silver crystallites having a mean diameter of from 0.02 to 0.4 $\mu$m in the case of the catalysts of the invention while catalysts which have been obtained by the customary processes display a morphology of the silver surface having a glass-like coating of silver crystallites which have a mean diameter of from 0.7 to 2 $\mu$m.

The catalysts of the invention can be used, for example, for preparing alkylene oxides by vapour-phase oxidation of olefins using air or other gases containing molecular oxygen. Examples of alkylene oxides are ethylene oxide, propylene oxide, 1,2-butylene oxide and 2,3-butylene oxide, preferably ethylene oxide. Examples of olefins which can be used for this purpose are ethylene, propylene, 1,2-butylene and 2,3-butylene, preferably ethylene. The invention thus also provides for the use of the catalysts of the invention for the above-described preparation of alkylene oxides.

This use according to the invention is made particularly advantageous in terms of the alkylene oxide yield by the surprisingly high activity and high selectivity. Thus, an operating temperature of from 160 to 230° C., preferably from 180 to 220° C., can be set in the preparation of ethylene oxide using the catalysts of the invention while customary operating temperatures in processes of the prior art are from 230 to 260° C. The selectivity for the preparation of ethylene oxide, for example, is about 83–84%.

As a result of the lower operating temperature, the formation of undesirable by-products is suppressed when using the catalysts of the invention. Likewise, the formation of hot spots in the catalyst bed is suppressed, so that the safety of the process for preparing alkylene oxides is improved at the same time.

The predecomposition and activation according to the invention of the catalyst of the invention proceeds under extremely mild conditions which lead to the above-described specific properties of the catalysts of the invention. In contrast to this, in the case of the conventional processes of uncontrolled decomposition and activation of silver-containing supported catalysts, the strongly exothermic combustion of carbon to carbon dioxide catalysed in an uncontrolled manner by the silver present makes it impossible to avoid localized very high temperatures because of the lack of temperature and oxygen control. Such irregularities in the preparation of the catalyst have a very adverse effect on the structure of the silver crystals which are responsible for the catalytic activity. The addition according to the invention of nitrate ions results, compared with EP '446, in a further increased controlled decomposition which further suppresses the agglomeration of the silver crystallites in favour of smaller silver particles.

In the preferred process variant in which the catalyst intermediate of the invention is used and is activated in the alkylene oxide reactor, a further important advantage of the present invention is shown: the very critical handling of activated catalysts which is known to every person skilled in the art, for example during storage, during transport or during introduction into the reactor, becomes unnecessary. At the same time, all possible irreversible disadvantageous influences which occur when handling activated catalysts are ruled out, so that according to the preferred process variant catalysts according to the invention reach the intended use in a fully active, completely unimpaired state.

EXAMPLE 1

Preparation of Silver Lactate 1600 g of $AgNO_3$, German Pharmacopoeia 7, were dissolved while stirring in 4000 ml of $H_2O$ in a 10 l glass beaker. A sodium hydroxide solution was prepared from 420 g of sodium hydroxide, analytical reagent, dissolved in 4000 ml of distilled $H_2O$. The silver hydroxide was precipitated over a period of about 2 hours by slow dropwise addition of the sodium hydroxide solution to the $AgNO_3$ solution. The precipitated silver hydroxide was washed free of nitrate in the same vessel using 4000 ml of distilled $H_2O$ each time (washed about 15 times). The presence of nitrate was tested by taking a sample of the washings and, in a test tube, carefully running a 0.5% strength diphenylamine solution in concentrated sulphuric acid down the side of the tube to form a layer under the sample. If a blue ring appeared at the interface, washing had to be continued. The nitrate test could also be carried out by means of analysis strips from Merck. Detection limit: less than 10 ppm of $NO_3^-$. The silver hydroxide was then filtered off with suction and pressed firmly so that little moisture remained in the filter cake.

1600 mg of 90% strength lactic acid (L+content>85%) were placed in a 5000 ml glass beaker. The lactic acid was preheated to about 50° C. and the freshly precipitated and moist silver hydroxide was added a little at a time while stirring and dissolved. During the dissolution procedure, the temperature should not exceed 80° C. Only after all the silver hydroxide had dissolved was a little hydrogen peroxide (35% strength, about 2–10 ml) added at from 80 to 85° C. until the silver lactate solution had a clear yellow colour. Yield: about 3470 g of silver lactate containing about 30% of silver.

The warm solution was poured onto a VA steel sheet and covered; the silver lactate became solid on cooling. The silver lactate was stored in a dark container.

EXAMPLE 2

Preparation of Catalyst A (Comparison)

In a 600 ml glass beaker, 200 g of silver lactate from Example 1 were admixed with 3 ml of 35% strength $H_2O_2$ and melted at about 70° C. 0.96 g of $Ba(OH)_2.8 H_2O$, 95 mg of $Cs_2CO_3$ and 150 mg of $K_2CO_3$ were added to this melt. 200 ml of a commercial $\alpha$-$Al_2O_3$ support having a specific surface area of 0.82 $m^2$/g (support A) were impregnated with the silver lactate solution obtained. After allowing excess silver lactate solution to drip off, the impregnated support was dried under nitrogen at about 80° C. in a convection oven for 2 hours. The residual oxygen content remained under 100 ppm during this procedure.

After drying, the temperature was increased to 220° C. over a period of 2 hours and then held for 2 hours. The material was then heated at a heating rate of 100° C./h to 450° C., still under nitrogen, and this temperature was likewise held for one hour and the material was subsequently cooled to 70–80° C. This intermediate which still contained about 3% by weight of carbon was placed in the experimental reactor. Nitrogen was passed through the reactor (space velocity: 200–1000 l/h) and the temperature was increased to 150° C. by means of the heating medium. The residual oxygen in the nitrogen remained below 100 ppm during this procedure.

Oxygen was then metered into the inert gas being fed into the reactor so that the oxygen concentration at the inlet was from 0.4 to 6% by volume. The formation of $CO_2$ was followed by analysis. The $CO_2$ content was not allowed to exceed 1% by volume. Corresponding to the $CO_2$ content, the temperature was increased by about 5° C./h. The metered addition of oxygen was likewise increased by about 1% by volume/h. After reaching a final temperature of 240° C. and an oxygen content of 21% by volume, the activation of the intermediate was completed for from 4 to 6 hours, after which the $CO_2$ content had dropped to below 0.1% by volume. The temperature in the reactor was reduced to 160° C. and the gas mixture required for the reaction to form ethylene oxide was passed over the catalyst. After a conditioning time of about 48 hours, the catalyst prepared in this way reached its final activity and selectivity. The catalyst prepared in this way was designated as A. The experimental results are shown in Table 1.

EXAMPLE 3

Preparation of Catalyst B

A catalyst was prepared as in Example 2. Apart from the salts of barium, caesium and potassium, an additional 10 g of silver nitrate was added to the silver lactate.

EXAMPLE 4

Preparation of Catalyst C (Comparison)

A catalyst was prepared as in Example 2. Another, likewise commercially available $\alpha$-$Al_2O_3$ support having a specific surface area of 0.80 $m^2$/g (support B) was impregnated with the solution.

EXAMPLE 5

Preparation of Catalyst D

A catalyst was prepared as in Example 4 using the support B. Apart from the salts of barium, caesium and potassium, an additional 10 g of silver nitrate were added to the silver lactate.

EXAMPLE 6

(Use Example)

The experimental laboratory reactor comprised an oil-heated metal tube having an internal diameter of 20 mm and a length of 500 mm. This reactor was charged first with 20 ml of inert material and subsequently with 170 ml of catalyst. The laboratory experiments were carried out at atmospheric pressure. The analytical monitoring of the reactor product gas stream was carried out continuously by means of a process gas chromatography. The space velocity was: 250 parts by volume of gas per part by volume of catalyst and hour. The gas mixture used for the gas-phase oxidation over the catalyst consisted of:

| | |
|---|---|
| $C_2H_4$ | 30% by volume |
| $O_2$ | 8% by volume |
| $N_2$ + inerts | 62% by volume |

1–2 ppm of 1,2-dichloroethane as inhibitor were added to the gas mixture used.

In an industrial reactor, the $N_2$ content of the gas mixture is mostly replaced by methane. There, the gas mixture consists, for example, of 30% by volume of $C_2H_4$, 8% by volume of $O_2$, 50% by volume of $CH_4$ and 12% by volume of $N_2$+inerts.

TABLE 1

| Catalyst | Temperature (° C.) | EOX (% by vol.)* | Selectivity (%) |
|---|---|---|---|
| A | 195 | 2.22 | 82.86 |
| A | 205 | 2.20 | 83.11 |
| B | 195 | 2.26 | 83.19 |
| B | 205 | 2.20 | 83.50 |
| C | 190 | 2.26 | 82.80 |
| C | 205 | 2.20 | 83.30 |
| D | 190 | 2.26 | 83.10 |
| D | 205 | 2.20 | 83.70 |

*EOX=Ethylene oxide content of the gas stream leaving the reactor; the selectivity at EOX contents set to the same value was employed for evaluating the catalysts.

After three months of operation, the catalysts displayed no loss in activity at the various temperatures indicated.

Catalysts having the nitrate content according to the invention in the treatment solution increase the selectivity by from 0.3 to 0.4 percentage points, which gives a considerable economic advantage in respect of the amount of EOX.

What is claimed is:

1. A process for preparing a supported catalyst comprising silver and optionally, a promoter, the process comprising the steps of:
   (a) treating a support having a specific surface area of less than or equal to 1.5 $m^2/g$ with a lactic acid comprising silver ions, nitrate ions and optionally, promoter metal ions to form a treated support,
   (b) (i) drying the treated support at a temperature of from about 50 to about 120° C. in an essentially oxygen-free atmosphere to form a dried treated support containing the lactic acid and nitric acid in free or ionic forms,
      (ii) predecomposing the lactic acid and the nitric acid in a first stage at a temperature of from about 140 to about 220° C. in an essentially oxygen-free atmosphere, and
      (iii) optionally, predecomposing the lactic acid and the nitric acid in a second stage at a temperature of from about 400 to about 500° C. in an essentially oxygen-free atmosphere, wherein the transition between the first and second stages of predecomposition is carried out with a heating rate of from about 70 to about 150° C. per hour, and wherein the predecomposition stage or stages form a supported catalyst intermediate,
   (c) activating the supported catalyst intermediate to form the supported catalyst by heating it in an oxygen-containing atmosphere at an increasing temperature of from 130 to a maximum of 450° C. with a heating rate of from about 3 to about 8° C. per hour, and at an increasing oxygen content of from about 0.5 to about 21% by volume, wherein the activation step generates a waste gas comprising a $CO_2$ content of less than or equal to 2% by volume.

2. The process according to claim 1, wherein the $CO_2$ content of the waste gas is less than or equal to 1% by volume.

3. The process according to claim 1, wherein the essentially oxygen-free atmosphere of the drying and predecomposition steps contains less than or equal to 100 ppm by volume of $O_2$.

4. The process according to claim 1, wherein from 1 to 30 mol % of the nitrate ions or the nitric acid is present per 100 mol % of the lactic acid.

5. The process according to claim 1, wherein the activation of the supported catalyst intermediate in step (c) is carried out in a reactor usable for preparing an alkylene oxide.

6. The process according to claim 1, wherein the predecomposition and activation steps are carried out under pressure.

7. The process according to claim 1, wherein the lactic acid comprises a racemate containing essentially equal amounts of two enantiomers.

8. The process according to claim 1, wherein at least 50% by weight of the lactic acid is in the L(+) form.

9. The process according to claim 8, wherein at least 80% by weight of the lactic acid is in the L(+) form.

10. The process according to claim 1, wherein the lactic acid further comprises a soluble, readily decomposable, and non-reducing organic compound.

11. A supported catalyst prepared by the process according to claim 1.

12. The supported catalyst according to claim 11, wherein the promoter is present and is an alkaline earth metal compound, an alkali metal compound, or a mixture thereof.

13. The supported catalyst according to claim 12, wherein the alkaline earth metal is calcium, strontium, barium, or a mixture thereof, and the alkali metal is lithium, sodium, potassium, rubidium, caesium, or a mixture thereof.

14. The supported catalyst according to claim 13, wherein the promoter is a compound of barium, caesium, potassium, or a mixture thereof.

15. A process for preparing a supported catalyst intermediate comprising silver and optionally, a promoter, the process comprising the steps of:
   (a) treating a support having a specific surface area of less than or equal to 1.5 $m^2/g$ with a lactic acid comprising silver ions, nitrate ions and optionally, promoter metal ions to form a treated support,
   (b) (i) drying the treated support at a temperature of from about 50 to about 120° C. in an essentially oxygen-free atmosphere to form a dried treated support containing the lactic acid and nitric acid in free or ionic forms,
      (ii) predecomposing the lactic acid and the nitric acid in a first stage at a temperature of from about 140 to about 220° C. in an essentially oxygen-free atmosphere, and
      (iii) optionally, predecomposing the lactic acid and the nitric acid in a second stage at a temperature of from about 400 to about 500° C. in an essentially oxygen-free atmosphere, wherein the transition between the first and second stages of predecomposition is carried out with a heating rate of from about 70 to about 150° C. per hour, and wherein the predecomposition stage or stages form the supported catalyst intermediate, (c) cooling the supported catalyst intermediate in an essentially oxygen-free atmosphere to a temperature of less than or equal to about 80° C.

16. A supported catalyst intermediate prepared by the process according to claim 15.

17. A process for preparing an alkylene oxide, the process comprising the step of oxidizing an olefin with an oxygen-containing gas in the presence of the supported catalyst according to claim 11.

18. The process according to claim 17, wherein the alkylene oxide is ethylene oxide, propylene oxide, 1,2-butylene oxide, or 2,3-butylene oxide, and the olefin is ethylene, propylene, 1,2-butylene, or 2,3-butylene.

* * * * *

UNITED STATES PATENT AND TRADEMARK OFFICE
CERTIFICATE OF CORRECTION

PATENT NO.  : 6,087,299
DATED       : July 11, 2000
INVENTOR(S) : Grub, et. al.

It is certified that error appears in the above-indentified patent and that said Letters Patent is hereby corrected as shown below:

On the cover page, section [73] Assignee, "EC Erdolchemie GmbH" should be - - EC Erdölchemie - -.

In column 9, line 29, "101 glass" should be - -10 l glass - -.

In column 9, line 47, "1600 mg" should be - - 1600 g - -.

Signed and Sealed this

Tenth Day of April, 2001

*Attest:*

NICHOLAS P. GODICI

*Attesting Officer*     *Acting Director of the United States Patent and Trademark Office*